United States Patent
KenKnight

[19]

[11] Patent Number: 6,148,230
[45] Date of Patent: Nov. 14, 2000

[54] METHOD FOR THE MONITORING AND TREATMENT OF SPONTANEOUS CARDIAC ARRHYTHMIAS

[75] Inventor: Bruce H. KenKnight, Maple Grove, Minn.

[73] Assignee: UAB Research Foundation, Birmingham, Ala.

[21] Appl. No.: 09/016,463

[22] Filed: Jan. 30, 1998

[51] Int. Cl.$^7$ .................................................. A61B 5/0452
[52] U.S. Cl. ........................................... 600/516; 600/509
[58] Field of Search ..................................... 600/509, 508, 600/515, 518, 523, 516; 607/32, 119; 128/898

[56] References Cited

U.S. PATENT DOCUMENTS

| | | | |
|---|---|---|---|
| 5,230,337 | 7/1993 | Dahl et al. | 607/5 |
| 5,313,953 | 5/1994 | Yomtov et al. | 600/508 |
| 5,314,430 | 5/1994 | Bardy | 607/5 |
| 5,331,966 | 7/1994 | Bennett et al. | 128/696 |
| 5,366,486 | 11/1994 | Zipes et al. | 607/5 |
| 5,433,730 | 7/1995 | Alt | 607/5 |
| 5,447,519 | 9/1995 | Peterson | 607/5 |
| 5,560,369 | 10/1996 | McClure et al. | 128/704 |
| 5,620,471 | 4/1997 | Duncan | 607/14 |

FOREIGN PATENT DOCUMENTS

| | | | |
|---|---|---|---|
| 0 472 411 A1 | 2/1992 | European Pat. Off. | A61B 5/07 |
| 0 554 208 A2 | 8/1993 | European Pat. Off. | A61B 5/0452 |

OTHER PUBLICATIONS

International Search Report for International Application No. PCT/US 99/01594, dated May 7, 1999.

*Primary Examiner*—Kennedy Schaetzle
*Attorney, Agent, or Firm*—Myers Bigel Sibley & Sajovec

[57] ABSTRACT

An implantable apparatus for the detection and monitoring of spontaneous cardiac electrogram features in a comprises a cardiac monitoring device and a plurality of subcutaneous cardiac sensing electrodes electrically connected to the monitoring device. The sensing electrodes are configured for sensing cardiac electrogram features when implanted in spatially separate locations in a patient. A storage device contained within the monitoring device is operably associated with the subcutaneous electrodes and stores the cardiac electrogram features. Preferably, the plurality of subcutaneous electrodes are carried by a single elongate lead. A downloading device such as telemetry apparatus or transcutaneous electrical connectors may be provided so that the stored information can be downloaded to a separate apparatus external to the patient. In a preferred embodiment, the apparataus is a defibrillator. Methods of using such apparatus are also disclosed.

5 Claims, 2 Drawing Sheets

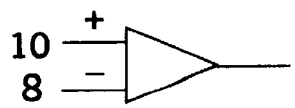
FIG. 3A
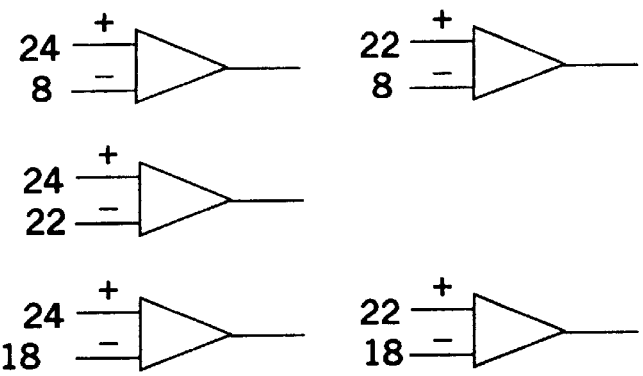
FIG. 3B
FIG. 4
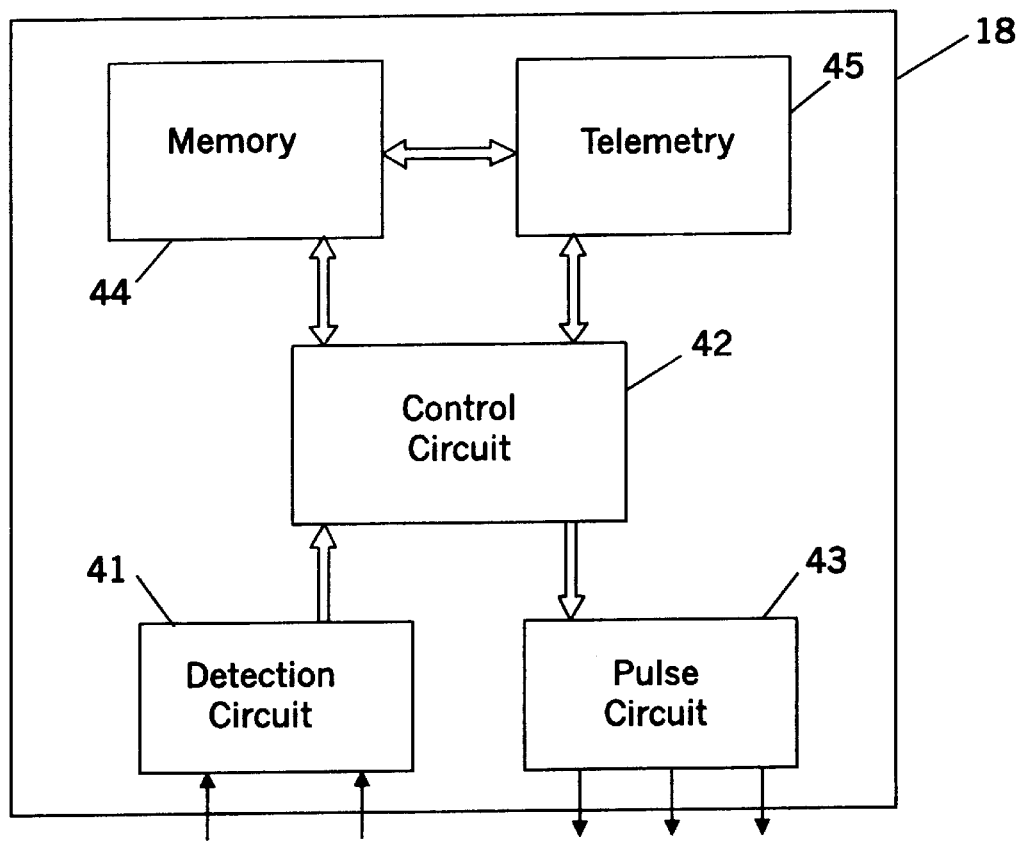

METHOD FOR THE MONITORING AND TREATMENT OF SPONTANEOUS CARDIAC ARRHYTHMIAS

FIELD OF THE INVENTION

The present invention relates to an implantable device that monitors cardiac electrogram feature information, which information can be used to detect and predict the onset of spontaneous cardiac arrhythmias. The electrogram feature information is detected through subcutaneous electrodes. The device can incorporate a defibrillator or other therapeutic shock treatment apparatus for treating cardiac arrhythmias.

BACKGROUND OF THE INVENTION

Numerous different cardiac arrhythmias are treated through implantable devices. Arrhythmias that can be treated with such devices include atrial and ventricular fibrillation, as well as less pronounced arrhythmias. Since such devices typically contain their own power supply, it is desireable to accurately predict when a therapeutic electrical pulse should be administered so that unnecessary pulses can be avoided. It is also desireable to be able to predict arrythmias in advance of onset or at an early phase, before the arrythmia progresses to a serious stage such as ventricular fibrillation. Accordingly, almost all implantable arrhythmia treatment devices incorporate sensing electrodes and sensing circuitry.

Current sensing electrodes are positioned on the right side of the heart, at the end of the defibrillation lead. Such sensing electrodes collect little information on electrical activity in the left ventricle. Because most arrhythmias originate in the left ventricle, obtaining left ventricle electrical information is highly desireable to providing an indication of risk of arrhythmia. In addition, spatial distribution of sensing electrodes (i.e., separating the electrodes in different locations) is also important, because spatially separate electrodes gather information from a greater volume of heart tissue. But, it is undesireable to place an electrode in the left ventricle because of the risk of clott formation on the catheter, leading to stroke.

In view of the foregoing, there is a continued need for new sensing electrode configurations and techniques that can be employed in implantable arrhythmia treatment apparatus.

SUMMARY OF THE INVENTION

A first aspect of the present invention is an implantable apparatus for the detection and monitoring of spontaneous cardiac electrogram features in a patient. In a preferred embodiment, the apparatus is a defibrillator. The apparatus comprises an implantable cardiac monitoring device and a plurality of subcutaneous cardiac sensing electrodes electrically connected to the monitoring device. The sensing electrodes are configured for sensing cardiac electrogram features when implanted in spatially separate locations in a patient. A storage device contained within the monitoring device is operably associated with the subcutaneous electrodes and stores the cardiac electrogram features. Preferably, the plurality of subcutaneous electrodes are carried by a single elongate lead. A downloading device such as telemetry apparatus or transcutaneous electrical connectors may be provided so that the stored information can be downloaded to a separate apparatus external to the patient.

A second aspect of the present invention is a method for detecting cardiac electrogram features in a patient in need thereof. The method comprises providing a plurality of subcutaneous sensing electrodes implanted in spatially separate locations in the patient, providing an implantable cardiac monitoring device operably associated with the subcutaneous sensing electrodes, detecting cardiac electrogram features through the plurality of sensing electrodes, and then storing the detected cardiac electrogram features in the monitoring device. The detected information can be used to administer an appropriate therapeutic electrical pulse to the patient.

The foregoing and other objects and aspects of the present invention are explained in detail in the drawings herein and the specification set forth below.

BRIEF DESCRIPTION OF THE DRAWINGS

FIG. 3A schematically illustrates a differential amplifier that is connected to sensing electrodes of FIG. 1 in a prior art configuration;

FIG. 3B schematically illustrates differential amplifiers that are connected to sensing electrodes of FIG. 1 in various configurations of the present invention; and FIG. 4 schematically illustrates an apparatus of FIG. 1, showing the relationship between various circuits.

DETAILED DESCRIPTION OF THE PREFERRED EMBODIMENTS

The terms "defibrillator", defibrillate" and defibrillation as used herein are intended to encompass cardioverter, cardiovert, and cardioversion, along with any other methods and apparatus that provide for a therapeutic treatment pulse to the heart of a subject, such as pacer, pace, pacing.

The term "subcutaneous" as used herein means outside the rib cage, and outside the chest cavity. In general, subcutaneous sensing electrodes described herein are positioned on the thorax of the patient, preferably on the left side and on the ventral surface (that is, on the chest). The subcutaneous electrodes may be carried by the same lead or different leads (preferably the same). The electrodes are preferably positioned at or below the level of the collar bone, and at or above the level of the xiphoid process, and are preferably positioned on the left side of the thorax.

The term "treatment pulse" as used herein refers to any type of treatment pulse, including low energy treatment pulses (e.g., under 8 joules for ventricular pulses; under 4 joules for atrial pulses) and high energy treatment pulses (e.g., 8 joules or more for ventricular pulses; 4 joules or more for atrial pulses). The pulses may be in pacing pulses including antitachycardia pacing, cardioversion pulses, defibrillation pulses, etc. The pulses may be delivered in any form including single or multiple pulses, sequential pulses, pulse trains, combinations thereof, etc.

The phrase "likelihood of occurrence of a spontaneous cardiac arrhythmia" is intended to include both situations where a cardiac arrhythmia has not yet occurred but is likely to occur in the future, and where a cardiac arrhythmia has occurred and is continuing.

Figure 1:
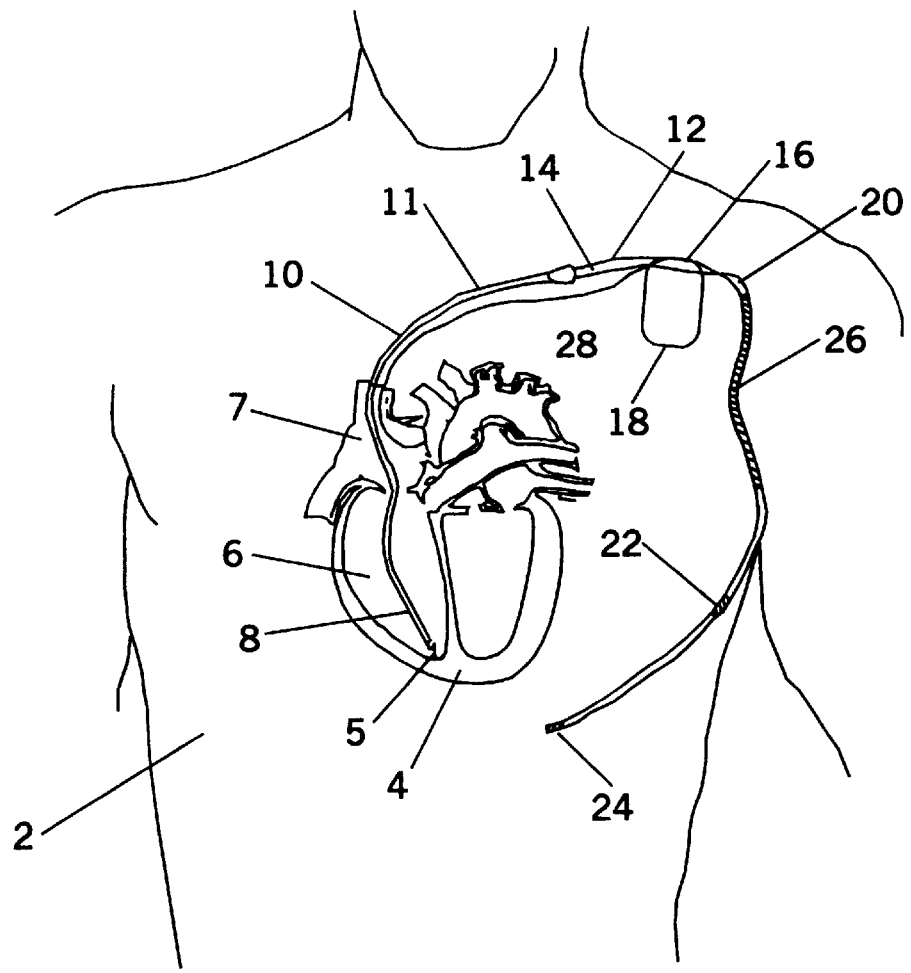
FIG. 1 illustrates an apparatus of the present invention as implanted in the thorax of a patient.

An apparatus of the present invention is schematically illustrated in FIG. 1. The apparatus is illustrated implanted in the thorax 2 of a patient. As illustrated, the apparatus includes an implantable cardiac defibrillator 18 which serves as the implantable cardiac monitoring device. An elongate lead 20 carrying two subcutaneous cardiac sensing electrodes 22, 24 is electrically connected to the defibrillator, with the sensing electrodes configured for sensing cardiac electrogram features when implanted in spatially separate locations in a patient. The elongate lead includes a defibrillation electrode 26, which is optional but preferred.

The defibrillator is configured for implantation in the left pre-pectoral position, and the elongate lead is configured for extending from the xiphoid process of the sternum of the patient to the implantable cardiac arrhythmia monitoring device. In general, subcutaneous electrode 24 is configured on the lead for positioning adjacent the xiphoid process of the patient, and subcutaneous electrode 22 is configured on the lead for positioning adjacent the left axilla of the patient. Additional subcutaneous sensing electrodes positioned on the lead proximal and/or distal to electrode 22 may be included if desired, and additional defibrillation electrodes may be positioned on the lead both proximal and/or distal to defibrillation electrode 26.

An elongate transveneous catheter 11 connected to the defibrillator 18 by yoke 15 to single conductors 12, 14 is flexibly configured for insertion into the heart 4 of the patient through the right atrium 7 and into the right ventricle 6. The catheter carries a distal, right ventricle electrode 8 and a proximal electrode 10. The proximal electrode 10 may be configured for positioning in any suitable location, such as the right atrium or superior vena cava. An additional, right atrium pacing and sensing electrode 28 is also illustrated, which electrode is optional but preferred. In general, at least one defibrillation electrode is included on the transveneous catheter, which may be inserted into the right atrium, the right ventricle, the coronary sinus or a peripheral vein, etc. The defibrillation pulse is preferably administered by one or more pair of electrodes: the complementary electrode (or additional electrodes) may be positioned in any suitable location, such as on the same or a different transvenous catheter, as a patch electrode on the outer surface of the heart, on the outer surface of the defibrillator (an "active can" electrode), on the lead carrying the subcutaneous sensing electrodes, etc.

Figure 2:
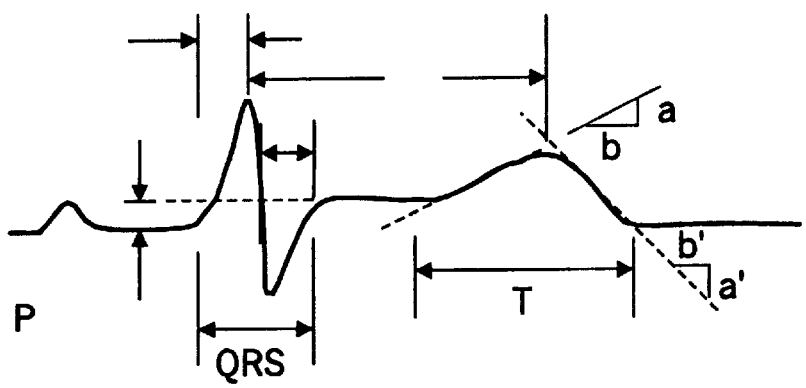
FIG. 2 illustrates a cardiac waveform, with the various components and features thereof that may be detected in accordance with the present invention.

The circuitry within housing 18 is schematically illustrated in FIG. 4. A detection circuit is electrically connected to the sensing electrodes 22, 24 by lines 22', 24', and the defibrillation electrodes 8, 10, 26 are electrically connected to the pulse circuit 43 by lines 8', 10' 26'. The detection circuit may include or incorporate a cardiac electrogram feature detector, including but not limited to QT interval detectors, PR interval detectors, ST interval detectors, RT interval detectors, T wave duration detectors, QRS duration detectors, R wave morphology detectors, and T wave morphology detectors (various features being illustrated by the representative cardiac electrogram set forth as FIG. 2). The detection circuit 41 is operably associated with control circuit 42, which is in turn associated with the pulse circuit 43 for delivering a treatment pulse through the defibrillation electrodes. Numerous different detection circuitries are known, and may be employed or modified to carry out the present invention. See, e.g., U.S. Pat. Nos. 5,560,369; 5,447, 519; 5,314,430; 5,366,486; and 5,620,471(the disclosures of which are incorporated herein by reference). The pulse circuit typically includes a capacitor and capacitor charger, as is known in the art.

In the embodiment illustrated in FIG. 1, the treatment pulse would be a ventricular defibrillation pulse, but any other type of treatment pulse as discussed above could be delivered, through the same or a different electrode configuration (as also discussed above).

A memory circuit 44 serving as a storage means is contained within the defibrillator and is operably associated with the sensing electrodes through the control circuit 42 for storing the cardiac electrogram features, and is operably associated with a telemetry circuit 45. The detection circuit 41 may be considered as part of the storage means in the illustrated embodiment, but is not critical thereto. In general, any memory device or circuit with or without a corresponding detection circuit and intervening processing circuit may serve as the storage means. The electrical activity may be stored in analog or digital form; the electrical activity may be stored as raw electrical data or as features or information derived from raw electrical data. The memory and telemetry circuits can be implemented in accordance with known techniques (see, e.g., U.S. Pat. No. 5,560,369).

Any suitable sensing electrode configuration can be employed with the detector, with at least one and preferably at least two sensing electrode carried by the subcutaneous lead(s). FIG. 3A illustrates an electrode configuration of the prior art, in which electrodes 8 and 10 are employed in the illustrated position as the sensing electrodes. In the present invention, suitable electrode configurations for the sensing electrodes include electrodes 24 and 8; electrodes 22 and 8; electrodes 24 and 22; electrodes 24 and 18; and electrodes 22 and 18. Where defibrillator 18 is designated as the electrode, the electrode is on the outer surface of the defibrillator (referred to as an "active can" electrode). Polarity is not critical and may be reversed from that indicated.

The defibrillator may also include a telemetry circuitry 45 (see FIG. 4) or tanscutaneous electrical connectors that serve as downloading means operatively associated with the storage means for transferring stored information on the electrical activity of the heart of the patient from the implantable cardiac arrhythmia monitoring device to a separate apparatus external to the patient. Thus the present invention can be used to detect arrhythmia, and then download feature and arrhythmia information and conduct an analysis to identify features that correlate with the onset of arrhythmia. The information can be used to reprogram or modify the device, or the device may auto-learn over time.

As will be appreciated by those skilled in the art, numerous circuitry configurations may be employed. The power supply may include a single capacitor, and the control circuit may be configured so that multiple components of the pulse are generated by the discharge of the single capacitor. The power supply may include a first and second capacitor, with the control circuit configured so that multiple components of the pulse are generated by the discharge of different capacitors. Multiple capacitors may be yoked together.

Systems as described above may be implanted in a patient by conventional surgical techniques, or techniques readily apparent to skilled surgeons in ligyht of the disclosure provided herein, to provide an implanted system.

Additional features can be added to the invention without affecting the function of the invention and result thereof. Such additional features include, but are not limited to, safety features such as noise suppression or multiple wave monitoring, verification checking to reduce false positives, precardiioversion warning, programmed delayed intervention, bipolar configured sensing electrodes, intermittently activated defibrillation detection to reduce energy drain, switching to minimize lines from the pulse generator, etc.

In use, the apparatus described above provides a therapeutic method that includes detecting cardiac electrogram features in a patient in need thereof. In overview, the method comprises providing a plurality of subcutaneous sensing electrodes implanted in spatially separate locations in the patient; providing an implantable cardiac defibrillator operably associated with the subcutaneous sensing electrodes; detecting cardiac electrogram features through the plurality of sensing electrodes; providing at least one elongate transveneous catheter inserted into the heart of the patient, the catheter connected to the defibrillator and carrying at least one defibrillation electrode; detecting electrical activity of the heart of the patient through the subcutaneous sensing electrodes; determining the likelihood of a spontaneous cardiac arrhythmia from the detected electrical activity; and then administering a therapeutic pulse to the heart through the at least one defibrillation electrode upon the determination of a likelihood of occurrence of a spontaneous cardiac arrhythmia. As above, the therapeutic pulse may be an atrial or ventricular therapeutic pulse. The method may further comprise the step of storing the detected cardiac electrogram features in the defibrillator, and then downloading the stored electrical activity to an external device. The stored electrical activity may be analyzed following the downloading step, and a therapeutic recommendation generated for managing cardiac arrhythmia for the patient based on the stored, downloaded, electrical activity.

The foregoing is illustrative of the present invention, and is not to be construed as limiting thereof. The invention is defined by the following claims, with equivalents of the claims to be included therein.

What is claimed is:

1. A method for detecting cardiac electrogram features in a patient in need thereof, comprising:

providing a plurality of subcutaneous sensing electrodes implanted in spatially separate locations in said patient, wherein said plurality of subcutaneous electrodes are carried by a single elongate lead;

providing an implantable cardiac monitoring device operably associated with said subcutaneous sensing electrodes;

detecting cardiac electrogram features through said plurality of sensing electrodes; and storing said detected cardiac electrogram features in said monitoring device to provide stored electrical activity; and extending said elongate lead from the xiphoid process of the sternum of said patient to a cardiac monitoring device implanted in the left pre-pectoral position in said patient.

2. A method according to claim 1, further comprising the step of downloading said stored electrical activity to a separate apparatus external to said patient.

3. A method according to claim 2, further comprising the steps of:

analyzing said stored electrical activity following said downloading step; and then generating a therapeutic recommendation for managing cardiac arrhythmia for said patient based on said stored electrical activity.

4. A method according to claim 1, further comprising positioning one of said subcutaneous electrodes adjacent the xiphoid process of the patient, and another of said subcutaneous electrodes adjacent the left axilla of the patient.

5. A method according to claim 1, wherein said detecting step comprises the step of detecting an event selected from the group consisting of QT interval, PR interval, ST interval, RT interval, T wave duration, QRS duration, R wave morphology, and T wave morphology.

* * * * *